(12) United States Patent
St. Clair et al.

(10) Patent No.: US 8,575,429 B2
(45) Date of Patent: *Nov. 5, 2013

(54) PLANT SEED MIXTURES

(75) Inventors: Gregory St. Clair, Hilliard, OH (US); Rex R. Raque, Galena, OH (US)

(73) Assignee: Crop Protection Services, Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/196,456

(22) Filed: Aug. 2, 2011

(65) Prior Publication Data

US 2011/0284401 A1    Nov. 24, 2011

Related U.S. Application Data

(63) Continuation of application No. 10/462,540, filed on Jun. 16, 2003, now Pat. No. 7,994,400.

(60) Provisional application No. 60/403,978, filed on Aug. 16, 2002.

(51) Int. Cl.
*A01H 5/10*    (2006.01)
*B65D 30/00*    (2006.01)

(52) U.S. Cl.
USPC ............................ 800/295; 800/300; 383/127

(58) Field of Classification Search
None
See application file for complete search history.

(56) References Cited

U.S. PATENT DOCUMENTS

| | | |
|---|---|---|
| 2,323,746 A | 7/1943 | Woolf et al. |
| 4,390,452 A | 6/1983 | Stevens |
| 4,495,724 A | 1/1985 | Kirkland et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,975,374 A | 12/1990 | Goodman et al. |
| 5,004,864 A | 4/1991 | Robertson et al. |
| 5,013,659 A | 5/1991 | Bedbrook et al. |
| 5,162,602 A | 11/1992 | Somers et al. |
| 5,253,302 A | 10/1993 | Massen |
| 5,276,268 A | 1/1994 | Strauch et al. |
| 5,545,821 A | 8/1996 | Wong et al. |
| 5,554,798 A | 9/1996 | Lundquist et al. |
| 5,561,236 A | 10/1996 | Leemans et al. |
| 5,704,160 A | 1/1998 | Bergquist et al. |
| 5,706,603 A | 1/1998 | Bergquist et al. |
| 5,764,819 A | 6/1998 | Orr et al. |
| 5,767,366 A | 6/1998 | Sathasivan et al. |
| 5,767,369 A | 6/1998 | Ryals et al. |
| 5,859,349 A * | 1/1999 | Raque ............................ 800/300 |
| 5,879,903 A | 3/1999 | Strauch et al. |
| 5,928,937 A | 7/1999 | Kakefuda et al. |
| 5,952,553 A | 9/1999 | Croughan |
| 5,977,441 A | 11/1999 | Oliver et al. |
| 5,994,621 A | 11/1999 | Raque |
| 6,084,155 A | 7/2000 | Volrath et al. |
| 6,114,609 A | 9/2000 | Beck et al. |
| 6,118,885 A | 9/2000 | Wadsworth et al. |
| 6,160,902 A | 12/2000 | Dickson et al. |
| 6,274,793 B1 | 8/2001 | Kobayashi et al. |
| 6,313,380 B1 | 11/2001 | Moots |
| 6,323,398 B1 | 11/2001 | Hicks |
| 6,339,184 B1 | 1/2002 | Smith |
| 6,346,657 B1 | 2/2002 | Steiger et al. |
| 6,350,938 B1 | 2/2002 | Threlkeld et al. |
| 6,353,157 B1 | 3/2002 | McClure et al. |
| 6,366,681 B1 | 4/2002 | Hutchins |
| 6,451,732 B1 | 9/2002 | Beckett et al. |
| 6,451,735 B1 | 9/2002 | Ottaway et al. |
| 6,455,157 B1 | 9/2002 | Simons |
| 7,994,400 B2 * | 8/2011 | St. Clair et al. ............... 800/312 |
| 2001/0016956 A1 | 8/2001 | Ward et al. |
| 2002/0129523 A1 | 9/2002 | Hunt |
| 2003/0056243 A1 | 3/2003 | Penner et al. |

FOREIGN PATENT DOCUMENTS

| | | |
|---|---|---|
| EP | 0 242 246 | 11/1992 |
| WO | WO 99/45514 | 9/1999 |
| WO | WO 00/34937 | 6/2000 |

OTHER PUBLICATIONS

The Arizona Crop Improvement Association.*
Holmberg (Successful Farming, Nov. 1999).*
Fisher (Soybean Digest, Apr. 1999).*
News Release (Sep. 10, 1998).*
'A Brief History of the "Feedsack"' [online]. Planet Patchwork, 1995-2005, [retrieved on May 16, 2005]. Retrieved from the internet: <URL: www.planetpatchwork.com/feedsack.htm>.
'A History of Packaging' [online]. Ohio State University [retrieved on May 16, 2005]. Retrieved from the internet:<URL: www.ohioline.osu.edu/cd-fact/0133.html>.
'Crops: Soybeans' [online]. Mississippi State University [retrieved on Jun. 1, 2005]. Retrived from the internet: URL:www.msucares.com/crops/soybeans/maturity.html>.
'Glossary' [online], [retrieved on Jun. 1, 2005]. Retrieved from the internet: <URL: www.vipsoybeans.org/v2Help/Vglossary.htm>.
'History' [online]. Curry Seed Company [retrieved on May 16, 2005]. Retrieved from the internet: <URL: www.curryseed.com/history/>.
'Yankee Gardener' [online]. Hart Seed Company [retrieved on May 16, 2005]. Retrieved from the internet: <URL: www.yankeegardener.com/seeds.html>.
"Marking time; Genetic markers identify herbicide-tolerant crops," *Successful Farming*, Nov. 1999.
"Meet Your Marker; yellow beans signal Roundup Ready fields," *Soybean Digest*, Apr. 1999.

(Continued)

*Primary Examiner* — Shubo (Joe) Zhou
*Assistant Examiner* — Keith Robinson
(74) *Attorney, Agent, or Firm* — Fish & Richardson P.C.

(57) ABSTRACT

Plant seed compositions are disclosed that comprise a herbicide-resistant variety as a major component and two or more additional varieties as minor components. One of the minor varieties is herbicide-resistant. Each variety is phenotypically distinguishable from all other varieties in the seed mixture.

16 Claims, No Drawings

(56) References Cited

OTHER PUBLICATIONS

"Old Yeller to the Rescue," *Ag Consultant*, Mar. 1999.
"Pathologist invents system to identify herbicide-resistant fields," *Seed Trade News*, Dec. 1998.
"Plant pathologist invents new way to identify Round-up resistant soybean plants from regular soybean plants," News Release, Sep. 10, 1998.
"Plant pathologist invents new way to identify Round-up resistant soybean plants from regular soybean plants," News Release, Jan. 19, 1999.
"Purity Requirements Threaten Marker Soybeans," *Seed Trade News*, Jun. 27, 1999.
"Roundup Ready Soybeans; New process identifies resistant beans," *Crop Protection Manager*, Feb. 1999.
"Royster Clark first to use yellow soybean marking system," *Crop Protection Manager*, Feb. 1999.
"Yellow Soybeans Get Green Light," *Seed Trade News*, Jul. 26, 2000.
Anand et al., "Performance of blends of soybean cyst nematode resistant and susceptible cultivars," *Crop Sci.*, 35:524-528.
Arizona Crop Improvement Association/Crop Standards/Soybeans; www.arizonacrop.org/crops/soybean.html, retrieved from the Internet Dec. 18, 2006.
Bregitzer et al., "Somaclonal variation in the progeny of transgenic barley," *Theor. Appl. Genet.*, 1998, 96:421-425.
Culpepper et al., "Weed management in glufosinate- and glyphosate-resistant soybean (*Glycine max*)," *Weed Technology*, 2000, 14:77-88.
Iowa Crop improvement Assoc., Iowa Seed Certification Requirements Handbook, pp. 47-49, 2000.
Murphy et al., "Compositional stability of an oat multiline," *Euphytica*, 1982, 31:33-40.
Orf et al., "Genetics of Soybean Agronomic Traits: I. Comparison of Three Related Recombinant Inbred Populations," Crop Sci., 1999, 39:1642-1651.
Sinclair (ed.), *Compendium of Soybean Diseases*, 1982, $2^{nd}$ edition, The American Phytopathological Society, p. 79.
Sodak Genetics Seed "Roundup Ready Soybeans," (SD1091RR variety, released in 2000).
Trimble and Fehr, "Mixtures of Soybean Cultivars to Minimize Yield Loss Caused by Iron-Deficiency Chlorosis," *Crop Science*, 1983, 23:691-694.
Williams, "The Inheritance of Certain Black and Brown Pigments in the Soybean ," *Genetics*, 1952, 37:208-215.
Authorized Officer David H. Kruse, International Search Report re PCT/US03/18808, mailed Nov. 2, 2005, 3 pages.

\* cited by examiner

PLANT SEED MIXTURES

CROSS-REFERENCE TO RELATED APPLICATION

This application is a Continuation application of, and claims benefit of priority under 35 U.S.C. §120 to, U.S. application Ser. No. 10/462,540, filed Jun. 16, 2003, issued as U.S. Pat. No. 7,994,400 on Aug. 9, 2011, which claims the benefit of priority under 35 U.S.C. §119(e) to U.S. Application No. 60/403,978, filed Aug. 16, 2002.

TECHNICAL FIELD

This invention relates to plant seed compositions, more particularly, seed mixtures containing herbicide-resistant varieties.

BACKGROUND

Herbicide-resistant plants are commonly used in production agriculture. Unfortunately, plants resistant to a particular herbicide are not visually distinguishable from similar plants that are sensitive to the same herbicide, especially during early stages of plant growth. This means there is a risk that the herbicide may be applied to sensitive plants, leading to complete loss of the crop. As varieties resistant to a particular herbicide become the dominant varieties, the incidence of misapplications may decrease. However, as other different herbicides and corresponding herbicide resistant varieties are developed and supplant older herbicides, the risk of misapplication can increase.

SUMMARY

The invention features an article of manufacture, comprising packaging material and plant seeds within the packaging material. The plant seeds can comprise about 90 to about 99.8 percent seeds of a first variety, about 0.1 to about 5 percent seeds of a second variety, and about 0.1 to about 5 percent seeds of a third variety. Plants of the first variety and the third variety exhibit resistance to the same herbicide and plants of the second variety exhibit sensitivity to the herbicide. Plants of the first, second, and third varieties are phenotypically distinguishable from each other. The plants of the first variety and the third variety can exhibit resistance to a herbicidal composition. The herbicidal composition can be a glyphosate, a phosphinothricin, or a glufosinate ammonium herbicidal composition. In some embodiments, plants of the first and third varieties exhibit resistance to a sulfonylurea or an imidazolinone herbicidal composition. In other embodiments, plants of the first and third varieties exhibit resistance to both a sulfonylurea herbicidal composition and an imidazolinone herbicidal composition. The plant seeds can be, e.g., *Brassica* seeds or soybean seeds.

Plants of the first variety can be phenotypically distinguishable from plants of the second variety by a difference in leaf color, and the plants of the third variety can be phenotypically distinguishable from plants of the first variety and second variety by a difference in leaf color or leaf number. The plants of the first variety can have green trifoliate leaves, plants of the second variety can have yellow trifoliate leaves, and the plants of the third variety can have yellow pentafoliate leaves. The plants of the first variety can have green trifoliate leaves, the plants of the second variety can have green variegated trifoliate leaves, and the plants of the third variety can have yellow pentafoliate leaves. The plants of the first variety can have green trifoliate leaves, the plants of the second variety can have yellow pentafoliate leaves, and the plants of the third variety can have yellow heptafoliate leaves. The plants of the second variety can be phenotypically distinguishable from plants of the first variety by the presence or absence of a fasciated stem, and the plants of the third variety can be phenotypically distinguishable from plants of the first and second varieties by a difference in leaf color and leaf number. The seeds of at least one of the varieties can have microparticles adhered thereto. The microparticles can be dual color microparticles. In some embodiments, seeds of at least one of the varieties has a seed coat color that differs from at least one other of the varieties, e.g., seeds of the first and third varieties have the same seed coat color and seeds of the second variety have a seed coat color that differs from the seed coat color of the first and third varieties.

The invention also features a composition comprising about 90 to about 99.5 percent seeds of a first variety, about 0.1 to about 5 percent seeds of a second variety and about 0.1 to about 5 percent seeds of a third variety, wherein plants of the first variety and the third variety exhibit resistance to the same herbicide, and plants of the second variety exhibit sensitivity to the herbicide, and wherein the first, second, and third varieties are phenotypically distinguishable from each other.

The invention also features a method for determining whether a group of crop plants is grown from a first generation seed composition or a second generation seed composition. The method comprises observing phenotypes of the group of plants before and after herbicide application; and determining that the group of plants is grown from a first generation seed composition if the number of phenotypic differences between the group of plants is greater before the herbicide application than after the herbicide application, or determining that the group of plants is grown from a second generation seed composition if the number of phenotypic differences in the group of plants is the same before and after herbicide application. The crop plants can be soybean plants.

The invention also features a method for determining whether a group of crop plants was grown from a first generation seed composition or a second generation seed composition. The method comprises observing phenotypes of the group of plants prior to herbicide application; and determining that the group of plants was grown from a first generation seed composition if about 0.1 to 5 percent of the plants differ in a first phenotypic marker from all other plants in the group, and about 0.1 to about 5 percent of the plants differ in a second phenotypic marker from all other plants in the group; or determining that the group of plants was grown from a second generation seed composition if about 0.05 percent to about 2.7 percent of the plants differ in a first phenotypic marker from all other plants in the group. The crop plants can be soybean plants.

The invention also features a method for determining whether a group of crop plants was grown from a first generation or a second generation seed composition. A first generation seed composition comprises about 90 to about 99.5 percent seeds of a first variety, about 0.1 to about 5 percent seeds of a second variety and about 0.1 to about 5 percent seeds of a third variety. A second generation seed composition comprises about 90 to about 99.95 percent seeds of the first variety, and about 0.05 to about 10 percent seeds of the third variety. The method comprises determining, prior to application of a herbicide to the plants, either that the group of plants was grown from a first generation seed composition when the expected proportion of a phenotypic marker associated with the second variety and the expected proportion of a phenotypic marker associated with the third variety are observed in the group of plants; or that the group of plants was grown from a second generation seed composition when significantly less than the expected proportion of a phenotypic marker associated with the second variety, and the expected proportion of a phenotypic marker associated with the third variety are observed among the group of crop plants. Plants of the first and third varieties exhibit resistance to the herbicide and are phenotypically distinguishable from each other. Plants of the second variety exhibit sensitivity to the herbicide and are phenotypically distinguishable from the first and third varieties.

The first generation seed composition can comprise about 95 to about 99.5 percent seeds of the first variety, e.g., about 97 to about 99.5 percent seeds of the first variety. The plant seeds can be soybean seeds. Plants of the first and third varieties can exhibit resistance to glufosinate or glyphosate. The phenotypic marker associated with the second variety can be leaf color. The phenotypic marker associated with the third variety can be the number of leaves per petiole.

In methods described herein, seeds of at least one of the varieties in a first generation seed composition can have a seed coat color that differs from the seed coat color of at least one of the other varieties in the first generation seed composition. Seeds of at least one of the varieties can have microparticles adhered thereto.

The invention also features a method for determining whether a group of crop plants has received an application of herbicide. The crop plants are grown from seeds comprising about 90 to about 99.5 percent seeds of a first variety, about 0.1 to about 5 percent seeds of a second variety and about 0.1 to about 5 percent seeds of a third variety. The method comprises determining that the crop plants have not received an effective application of herbicide when the expected percentage of the crop plants have a phenotypic marker associated with the second variety and the expected percentage of the plants have a phenotypic marker associated with the third variety; or have received an effective application of herbicide when significantly less than the expected percentage of the crop plants have a phenotypic marker associated with the second variety and the expected percentage of the crop plants have a phenotypic marker associated with the third variety. Plants of the first variety and third varieties exhibit resistance to the same herbicide and are phenotypically distinguishable from each other, and plants of the second variety exhibit sensitivity to the herbicide and are phenotypically distinguishable from the first and third varieties. Plants of the first and third varieties can exhibit resistance to glufosinate or to glyphosate. The plant seeds can be soybean seeds. The phenotypic marker associated with the second variety can be leaf color. The phenotypic marker associated with the third variety can be the number of leaves per petiole.

The invention also features a method of making an article of manufacture. The method comprises packaging plant seeds within a packaging material. The plant seeds comprise about 90 to about 99.8 percent seeds of a first variety, about 0.1 to about 5 percent seeds of a second variety, and about 0.1 to about 5 percent seeds of a third variety. Plants of the first variety and the third variety exhibit resistance to the same herbicide and plants of the second variety exhibit sensitivity to the herbicide. Plants of the first, second, and third varieties are phenotypically distinguishable from each other.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

DETAILED DESCRIPTION

The inventors have discovered novel compositions that comprise a mixture of seeds from multiple varieties of a single plant species. Typically, the composition contains three different varieties. A first variety constitutes the majority of seed in the composition, and the second and third varieties together constitute a minority of seed in the composition. Each of the varieties in the mixture can be distinguished from all other varieties in the composition on the basis of phenotypic markers. The first and third varieties exhibit resistance to a particular herbicide, but are phenotypically distinguishable from each other. The second variety is sensitive to the particular herbicide, and is phenotypically distinguishable from both the first and third varieties.

Such a seed composition is useful to farmers and agricultural companies such as seed companies or farm supply companies. A group of plants grown from such a composition permits one to identify fields that have not had any application of herbicide, e.g., by visual inspection for the presence of the second, herbicide-sensitive variety and actively growing weeds.

Seed Compositions

A plant seed composition of the invention contains seeds of at least three varieties. The proportion of each variety in a composition is measured as the number of seeds of a particular variety divided by the total number of seeds in the composition, and can be formulated as desired to meet requirements based on geographic location, choice of herbicide, and the like. The proportion of the first variety can be from about 85 percent to about 99.8 percent, e.g., 90%, 91%, 92%, 93%, 94%, 95%, 96%, 97%, 98%, or 99%. The proportion of the second variety can be from about 0.1 percent to about 5 percent, e.g., 0.5%, 1%, 2%, 3%, 4%, or 5%. The proportion of the third variety can be from about 0.1 percent to about 5 percent, e.g., 0.5%, 1%, 2%, 3%, 4%, or 5%. When large quantities of a seed composition are formulated, or when the same composition is formulated repeatedly, there may be some variation in the proportion of each variety due to sampling error. Sampling error is known from statistics. In the present invention, such sampling error typically is about ±5% of the expected proportion, e.g., 90%±4.5%, or 5%±0.25%. A seed composition can be formulated in a quantity of about 35 kilograms (kg) or more, about 100 kg or more, about 1,000 kg or more, about 10,000 kg or more, or about 50,000 kg or more.

Plants grown from seeds of the first variety exhibit resistance to a herbicide. Plants grown from seeds of the second variety are sensitive to the herbicide to which the first variety is resistant. Second variety plants are phenotypically distinguishable from plants of the first variety on the basis of one or more phenotypic markers. Plants grown from seeds of the third variety are resistant to the same herbicide as the first variety. Such plants, however, are phenotypically distinguishable from plants of the first variety, and are phenotypically distinguishable from plants of the second variety.

For example, a seed composition of the invention can be made from three soybean varieties. A first soybean variety can constitute 98.5% of the seeds in the composition and be glyphosate-resistant, with green trifoliate leaves. A second soybean variety can constitute 0.5% of the seed in the composition and be glyphosate-sensitive, with yellow trifoliate leaves. A third soybean variety can constitute the remaining 1% of the composition and be glyphosate-resistant, with yellow pentafoliate leaves. Thus, each of the three varieties is phenotypically distinguishable from all other varieties in the mixture. In addition, the major variety and one of the minor varieties exhibit resistance to the same herbicide.

Typically, a substantially uniform mixture of seeds of each of the varieties is conditioned and bagged in packaging material by means known in the art to form an article of manufacture. Such a bag of seed preferably has a package label accompanying the bag, e.g., a tag or label secured to the packaging material, a label printed on the packaging material or a label inserted within the bag. The package label indicates that the seeds therein are a mixture of varieties, e.g., three different varieties. The package label may indicate that plants grown from such seeds are suitable for determining whether initial and follow-up herbicide applications have been made to such plants. The package label also may indicate that the seed mixture contained therein permits detection if seed saved from the harvested crop is replanted in a subsequent growing season.

In some embodiments, a plant seed composition further comprises additional varieties, e.g., about 0.1 to about 5 percent seeds of a fourth variety. Plants grown from seeds of such additional varieties are phenotypically distinguishable from all other varieties in the composition, e.g., the first variety, second variety and third variety. Plants of such additional varieties may or may not exhibit resistance to the same herbicide as do plants of the first and third varieties.

Varieties in a seed composition of the invention typically have the same or very similar maturity, i.e., the same or very similar number of days from germination to crop seed maturation. In some embodiments, however, one or more varieties in a seed composition of the invention can have a different relative maturity compared to other varieties in the composition, i.e., the number of days from germination to mature seed for one variety in a composition is statistically significantly different from that of another variety in the composition. For example, the first variety in a composition of soybean seeds can be classified as belonging to the Group V relative maturity group, while the second variety can be classified in the Group I relative maturity group and the third variety can be classified in the Group V relative maturity group. As another example, the first variety in a composition of soybean seeds can be classified as belonging to the Group 0 relative maturity group, while the second variety can be classified in the Group I relative maturity group and the third variety can be classified in the Group II relative maturity group. The presence of varieties of different relative maturities in a seed composition can be useful when it is desired to reduce the amount of second and/or third variety seeds in the harvested crop. Relative maturity of a variety of a given crop species is classified by techniques known in the art.

A number of plant species are suitable for practicing the invention. Species that are naturally self-pollinated are particularly suitable, e.g., dicotyledonous species such as soybean, including natto and tofu soybeans, and rapeseed. Also suitable are vegetable crops or root crops such as potato, broccoli, peas, sweet corn, popcorn, tomato, beans (including kidney beans, lima beans, dry beans, green beans) and the like. Suitable plants include species from the genera *Arachis, Asparagus, Atropa, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Lactuca, Linum, Lupinus, Lycopersicon, Malus, Manihot, Majorana, Medicago, Nicotiana, Olea, Persea, Phaseolus, Pistachia, Pisum, Pyrus, Prunus, Raphanus, Ricinus, Senecio, Sinapis, Solanum, Theobromus, Trigonella, Vicia, Vitis*, and *Vigna*. See, e.g., U.S. Pat. No. 6,274,793.

In some embodiments, a seed composition of the invention contains varieties of different plant species, e.g., the first plant variety is soybean, the second plant variety is rapeseed, and the third plant variety is soybean.

Herbicides

The first and third plant varieties of the invention exhibit resistance to the same herbicide. A number of genes are available, both transgenic and non-transgenic, that confer herbicide resistance. Herbicide resistance is also sometimes referred to as herbicide tolerance. Genes conferring resistance to a herbicide that inhibits the growing point or meristem, such as an imidazolinone or a sulfonylurea can be suitable. Exemplary genes in this category code for mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS) resistant to inhibition by herbicides that are known to inhibit GS, e.g. phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Genes for resistance to glyphosate (sold under the trade name Roundup®) are also suitable. See, for example, U.S. Pat. No. 4,940,835 and U.S. Pat. No. 4,769,061. U.S. Pat. No. 5,554,798 discloses transgenic glyphosate resistant maize plants, in which resistance is conferred by an altered 5-enolpyruvyl-3-phoshoshikimate (EPSP) synthase gene. Such genes can confer resistance to glyphosate herbicidal compositions, including without limitation glyphosate salts such as the trimethylsulphonium salt, the isopropylamine salt, the sodium salt, the potassium salt and the ammonium salt. See, e.g., U.S. Pat. Nos. 6,451,735 and 6,451,732.

Genes for resistance to phosphono compounds such as glufosinate ammonium or phosphinothricin, and pyridinoxy or phenoxy propionic acids and cyclohexones are also suitable. See European application No. 0 242 246. See also, U.S. Pat. Nos. 5,879,903, 5,276,268 and 5,561,236.

Other suitable herbicides include those that inhibit photosynthesis, such as a triazine and a benzonitrile (nitrilase). See U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are herbicides that confer resistance to a protox enzyme. See, e.g., U.S. Patent Application No. 20010016956, and U.S. Pat. No. 6,084,155.

For example, soybean (*Glycine max*) is an important and valuable field crop. Soybean breeders develop stable, high yielding soybean varieties that are agronomically sound. To this end, soybean breeders have developed transgenic and non-transgenic varieties that possess resistance to certain herbicides. Exemplary glyphosate resistant soybean varieties include those disclosed in U.S. Pat. Nos. 6,353,157; 6,350,938; 6,346,657; 6,323,398 and 6,313,380. Additional herbicide resistant soybean varieties can be developed from a transgenic soybean line designated 40-3, which carries a gene conferring resistance to Roundup® herbicide.

Herbicide resistant wheat varieties have been developed. Exemplary herbicide resistant wheat varieties include those disclosed in U.S. Pat. No. 6,339,184. Herbicide resistant canola varieties are discussed in U.S. Pat. No. 5,545,821. Exemplary herbicide resistant rice varieties include those disclosed in U.S. Pat. No. 5,952,553.

Phenotypic Markers

Each variety in a seed composition possesses a phenotypic marker other than herbicide resistance that is associated with that variety, and which distinguishes that variety from other varieties in the composition, i.e., characterizes that variety relative to other varieties in the composition. Phenotypic markers permit each of the three varieties present in a seed composition to be distinguished during vegetative stages of growth. Generally, phenotypic markers permit varieties to be identified by visual inspection, although it is contemplated that phenotypic markers such as isozyme polymorphisms or nucleic acid polymorphisms can be used. In some embodiments, a phenotypic marker is a difference between two or more varieties in visible, near-infrared, or infrared radiation characteristics. Such a difference can permit varieties to be distinguished by remote sensing, e.g., satellite imaging. See, e.g., U.S. Pat. Nos. 5,764,819, 6,118,885, 6,160,902, 6,366,681 and 5,253,302. Phenotypic markers should be sufficiently stable to allow varieties to be distinguished despite variation in disease pressure, insect pressure, environment, or agronomic practices, recognizing that a phenotypic marker that is sufficiently stable in one geographic region may not be sufficiently stable in a different geographic region. Typically, a single marker is used to phenotypically distinguish each variety in the composition from all other varieties. It will be appreciated, however, that a variety can have two or more phenotypic differences from any other variety in the composition.

A number of phenotypic differences can be used to distinguish different varieties. For example, in soybean, one can incorporate phenotypic markers such as: leaf number per petiole (3, 5, 7, 9, or 11), leaf color (yellow, light green, medium green, or green), leaf color uniformity (uniform or variegated), cotyledon color (yellow or green), leaflet shape (rugose or lanceolate), or plant habit (determinate or indeterminate). Additional phenotypic markers include, without limitation, fasciated stem and dense pubescence. Table 1 summarizes some possible phenotypic combinations that can be used to distinguish between different soybean varieties. The numeral indicates the number of leaves per petiole present on the plant, e.g., 3L indicates three leaves, 5L indicates five leaves, and 7L indicates seven leaves. The letter "Y" indicates that the colors of the leaves are yellow.

TABLE 1

Herbicide Sensitive and Resistant Combinations of Soybean Phenotypes

| Herbicide Sensitive Combinations | Herbicide Resistant Combinations |
|---|---|
| 3LY combinations | 3LY combinations |
| 3LY yellow seed coat | 3LY yellow seed coat |
| 3LY brown seed coat | 3LY brown seed coat |
| 3LY black seed coat | 3LY black seed coat |
| 3LY green seed coat | 3LY green seed coat |
| 3LY Lanceolate leaves | 3LY Lanceolate leaves |
| 3L Variegated leaves | 3L Variegated leaves |
| 3L Lanceolate and Variegated leaves | 3L Lanceolate and Variegated leaves |
| 3LY rugose yellow seed coat | 3LY rugose yellow seed coat |
| 3LY rugose brown seed coat | 3LY rugose brown seed coat |
| 3LY rugose black seed coat | 3LY rugose black seed coat |
| 3LY rugose green seed coat | 3LY rugose green seed coat |
| 3LY rugose Lanceolate leaves | 3LY rugose Lanceolate leaves |
| 3L rugose Variegated leaves | 3L rugose Variegated leaves |
| 3L rugose Lanceolate, Variegated leaves | 3L rugose Lanceolate, Variegated leaves |
| 5LY combinations | 5LY combinations |
| 5LY yellow seed coat | 5LY yellow seed coat |
| 5LY brown seed coat | 5LY brown seed coat |
| 5LY black seed coat | 5LY black seed coat |
| 5LY green seed coat | 5LY green seed coat |
| 5LY Lanceolate leaves | 5LY Lanceolate leaves |
| 5L Variegated leaves | 5L Variegated leaves |
| 5L Lanceolate and Variegated leaves | 5L Lanceolate and Variegated leaves |
| 5LY rugose yellow seed coat | 5LY rugose yellow seed coat |
| 5LY rugose brown seed coat | 5LY rugose brown seed coat |
| 5LY rugose black seed coat | 5LY rugose black seed coat |
| 5LY rugose green seed coat | 5LY rugose green seed coat |
| 5LY rugose Lanceolate leaves | 5LY rugose Lanceolate leaves |
| 5L rugose Variegated leaves | 5L rugose Variegated leaves |
| 5L rugose Lanceolate, Variegated leaves | 5L rugose Lanceolate, Variegated leaves |
| 7LY combinations | 7LY combinations |
| 7LY yellow seed coat | 7LY yellow seed coat |
| 7LY brown seed coat | 7LY brown seed coat |
| 7LY black seed coat | 7LY black seed coat |
| 7LY green seed coat | 7LY green seed coat |
| 7LY Lanceolate leaves | 7LY Lanceolate leaves |
| 7L Variegated leaves | 7L Variegated leaves |
| 7L Lanceolate and Variegated leaves | 7L Lanceolate and Variegated leaves |
| 7LY rugose yellow seed coat | 7LY rugose yellow seed coat |
| 7LY rugose brown seed coat | 7LY rugose brown seed coat |
| 7LY rugose black seed coat | 7LY rugose black seed coat |

TABLE 1-continued

Herbicide Sensitive and Resistant Combinations of Soybean Phenotypes

| Herbicide Sensitive Combinations | Herbicide Resistant Combinations |
|---|---|
| 7LY rugose green seed coat | 7LY rugose green seed coat |
| 7LY rugose Lanceolate leaves | 7LY rugose Lanceolate leaves |
| 7L rugose Variegated leaves | 7L rugose Variegated leaves |
| 7L rugose Lanceolate, Variegated leaves | 7L rugose Lanceolate, Variegated leaves |

A phenotypic marker typically is genetically determined by nuclear or cytoplasmic inheritance. A phenotypic marker can be due to naturally occurring mutation(s) or can be conferred by a transgene. It is contemplated that a trait conferred by a plant virus can also be useful. It will be appreciated that some phenotypic markers may have some similarity to symptoms observed due to disease pressure, nutrient deficiency, or weather. For example, manganese deficiency may be observed on soybean plants in some geographic areas, e.g., well-drained neutral and alkaline soils with a high pH. Symptoms characteristic of manganese deficiency include yellow leaves. See *Compendium of Soybean Diseases*, J. B. Sinclair, ed., 2$^{nd}$ Edition, p. 79, The American Phytopathological Society (1982). The practitioner will recognize and take into account the possibility of such similarities when formulating seed compositions of the invention for a given geographic area.

Additional Markers

In some embodiments, seeds of a third variety in a composition of the invention have a seed coat color that differs from other varieties in the composition. Since non-herbicide resistant and herbicide resistant seeds often have a similar seed coat color and cannot be easily distinguished, a different seed coat color can be used to mark a composition as having a herbicide resistant variety. Furthermore, the resulting harvested crop contains seeds having the seed coat color of the third variety, thus marking the crop as containing herbicide resistant seeds. In addition, a farmer sometimes saves a portion of the harvested crop for use as seed to be replanting in subsequent growing seasons. Saved seeds are often conditioned and packaged by a seed conditioner before such replanting. The presence of seeds having different seed coat colors permits a seed conditioner to distinguish between herbicide resistant and non-herbicide resistant seed and thus condition herbicide resistant seed separately from non-herbicide resistant seed. The presence of seeds having the colors of the first and third varieties makes it apparent which conditioned seed lots are herbicide resistant.

In some embodiments, each variety in a seed composition has a different seed coat color. For example, a composition can have 99.9% seeds of a first variety having a tan seed coat color, 0.075% seeds of a second variety having a green seed coat color, and 0.025% seeds of a third variety having a black seed coat color. Another suitable seed coat color is brown. In other embodiments, seeds of the second and third varieties in a composition have the same seed coat color, which seed coat color differs from the seed coat color of the first variety in the composition. For example, the first variety can have a brown seed coat color, green leaves, and exhibit glufosinate resistance, the second variety can have a black seed coat color, yellow leaves, and exhibit glufosinate sensitivity, and the third variety can have a black seed coat color, variegated leaves, and exhibit glufosinate resistance.

In other embodiments, seeds of the first and second varieties in a composition have the same seed coat color, which seed coat color differs from the seed coat color of the third variety in the composition. In other embodiments, seeds of the first and third varieties in a composition have the same seed coat color, which seed coat color differs from the seed coat color of the second variety in the composition.

A seed composition having varieties with different seed coat colors can be useful to farmers and agricultural companies, since it permits identification of whether harvested seeds contain a particular herbicide resistance trait. For example, a seed composition containing seeds of a first variety having a tan seed coat color, seeds of a second variety having a green seed coat color, and seeds of a third variety having a black seed coat color, will result in a harvested crop that contains tan seeds and black seeds, thereby marking the crop as containing the particular herbicide resistance trait(s) carried by that seed composition. Thus, in another aspect, the invention features a method of marking a harvested crop. The method involves growing a seed composition of the invention, and harvesting a crop from plants that result from growing the composition.

In some embodiments, microparticles are used to mark one or more varieties in a seed composition. Microparticles adhered to individual seeds of a particular variety permit ready identification of that variety. A specific series of microparticle types can be used, each series adhered to seeds of a particular variety. Alternatively, a single type of microparticles can be used, such a type adhered to seeds of only one of the varieties in a seed composition. As another alternative, microparticles can be used to mark an individual article of manufacture, e.g., by adhering microparticles to packaging material or to a package label accompanying the article. In the case of a plurality of articles, microparticles can be combined with or adhered to a packaging or shipping container that contains the plurality of articles.

Microparticles can be combined with a binder, for instance an adhesive or coating formulation. Suitable binder materials are known. The resulting particle/adhesive mixture can, for example, then be applied to the surface of individual seeds for identification purposes.

A marked seed(s) can be observed to determine the presence or absence of microparticles. If the microparticles are visible to the naked eye, the examination may be performed without additional equipment. For microparticles that are not easily visualized by the naked eye, equipment such as a light microscope or a magnifying glass may be used. Typically, microparticles can be examined using a common 40× or 100× microscope.

The presence or absence of specific microparticles can be detected and recorded. An individual can perform the detection and recordation manually. Alternately, an automated system, e.g., a computerized system, can perform detection and recordation.

Microparticles having a single colored layer can be used, recognizing that certain colors may not be suitable for particular seed coat colors. For example, a tan microparticle would render identification difficult if the marked variety had a tan seed coat color. Microparticles having two colored layers can be used. Dual layer microparticles can often provide a sufficient diversity of color combinations. Alternatively, a 5-layered particle can be used. If desired, microparticles can include visual enhancers. Suitable visual enhancers include, without limitation, pearlescent colorant, glitter, metal flake pigments and glass microspheres. Visual enhancers can provide microparticles with a higher localized reflectance and a more characteristic appearance, making the colored layer(s) of a microparticle are more easily distinguishable. Visual enhancers can also further differentiate color layers of one type of microparticle from another type of microparticle. For example, a visual enhancer can be added to distinguish one secondary color (i.e., orange, green, and purple) from another secondary color.

As an alternative to visually distinguishable characteristics, the layer(s) of different types of microparticles may be distinguished by machine-readable characteristics. Machine-readable characteristics can include magnetic characteristics, infrared or ultraviolet absorption characteristics, infrared or ultraviolet reflection characteristics, or fluorescence or visible light transmission characteristics.

Methods

The invention also features a method of identifying fields containing crop plants grown from saved seeds. A seed composition of the invention contains seeds of the major variety and both minor varieties in the desired ratio, and can be referred to as first generation seeds for purposes of describing the method. First generation seeds give rise to plants having phenotypic differences that can be used to distinguish the various varieties, e.g. to distinguish the major variety from the minor varieties, and the minor varieties from each other. For example, a group of plants grown from first generation seeds, that have not had any application of herbicide or have had an ineffective application of herbicide, can be identified by the presence of herbicide-sensitive plants of the second variety. Actively growing weeds are also an indication of no application of herbicide, or an ineffective application of herbicide. After one or more effective applications of herbicide, such a group of crop plants can be identified by the absence of second variety plants. Moreover, the presence of plants of the third variety in such a group serves to confirm that the group contains herbicide-resistant plants, and is thus suitable for follow-up applications of herbicide if necessary.

At maturity, a crop can be harvested from a field containing a group of plants of the first and third varieties. If seed of the resulting harvested crop is saved for replanting in a subsequent growing season, it will contain seeds of the first and third varieties, but little or no seed of the second variety. Such saved seed can be referred to as second generation seeds for purposes of describing the method. A field containing a group of plants grown from second generation seeds is distinguishable from a field containing plants grown from first generation seeds, due to the absence of plants of the second variety.

Thus, the method involves observing phenotypes among a group of crop plants, grown from a seed composition of the invention, and concluding that the plants were grown from a first generation seed composition when, in the absence of an effective herbicide application, about 0.1 to about 5 percent of the plants have a first phenotypic marker distinguishing them from all other plants in the group and about 0.1 to about 5 percent of the plants have a second phenotypic marker distinguishing them from all other plants in the group. Observations may involve every plant in the field if desired. In the case of manual inspection of visually observable phenotypic differences, however, such observations generally involve a representative sample of the crop plants in the group. Typically, the number of crop plants observed is sufficiently large so that any subsequent conclusions about the percentage of second and/or third variety plants can be considered statistically significant at $p<0.05$.

One can conclude that the plants were grown from a first generation seed composition when, following one or more effective herbicide applications, about 0.1 to about 5 percent of the plants have a first phenotypic marker distinguishing them from all other plants in the group, and essentially no plants have a second phenotypic marker.

On the other hand, phenotypes can be observed among a group of crop plants grown from second generation seeds in a field prior to herbicide application, and it can be concluded that the plants were grown from a second generation seed composition (saved seed), when about 0.05% to about 5% of the plants are of the third variety, i.e., have a phenotypic marker distinguishing them from all other plants in the field. There will be essentially no crop plants of the second variety in such a field, i.e., having a second phenotypic marker. It is noteworthy that if saved seed is replanted, the proportion of the two types of plants will not change after herbicide application, because both varieties are herbicide-resistant. The percentage of plants of the third variety that are present in a field planted to saved seed will depend primarily upon two factors: the percentage of third variety seed present in the first generation seed composition and the ratio of third variety yield/first variety yield. For example, if first generation seed contains first, second, and third varieties in a proportion of about 98:1:1, and the first variety has a yield that is two fold greater than the third variety, then about 0.5% of the crop plants in a field grown from replanted seed will be of the third variety and will be phenotypically distinguishable from all other crop plants in the field.

In another aspect, the invention features a method for determining whether a group of crop plants has received an application of herbicide. The method involves observing phenotypes among the crop plants in a field, the plants having been grown by planting first generation seeds. The phenotypes can be observed as described herein, e.g., visually, by molecular biological assays, or by satellite imaging.

Based on the observed phenotypes, one can conclude that the crop plants have not received an effective application of herbicide when the expected proportion of the second variety phenotype and the expected proportion of the third variety are present. As discussed above, the presence of the second, herbicide-sensitive variety indicates that the field has not received an application of the herbicide to which the second variety is sensitive, or that if a herbicide was applied, it was not effective. On the other hand, one can conclude that the crop plants have received an effective application of herbicide when the proportion of the second variety phenotype among the group of crop plants in the field is significantly less than expected, e.g., essentially no crop plants have the second variety phenotypic marker. The expected proportion of the third variety phenotype is present under these conditions.

The compositions and methods of the invention are useful in that fields in need of an initial or follow-up application of herbicide can be identified. Even when a field is known to have had one application of herbicide, the compositions and methods are useful in determining if the initial herbicide application was effective. The presence of a significant number of plants in the field having a phenotypic marker characteristic of the second variety indicates that a follow-up herbicide application may be necessary, while the presence of plants of the third variety indicates that the field is suitable for spraying the particular herbicide (i.e., is not a field of conventional herbicide-sensitive plants).

A seed composition of the invention can permit farmers and seed companies to distinguish between an older herbicide-resistant variety and a newer herbicide-resistant variety in a geographic region, i.e., fields planted with a herbicide-resistant variety that has been on the market for a period of time and fields planted with a variety that has recently been introduced for sale and is resistant to the same herbicide. The older variety can be formulated during phase-out as the major proportion in a seed composition that contains two minor varieties, while the newer variety can be formulated as the only seed in a composition. Alternatively, the older variety can be sold as the only seed in a composition, while the newer variety can be formulated during phase-in as the major proportion in a seed composition that contains two minor varieties.

As another alternative, a newer variety can be formulated during phase-in as the major portion of a seed composition that contains second and third varieties, while an older variety can be sold as the major portion in a seed composition that contains a minor portion of a fourth variety. In this instance, the fourth variety can be either herbicide resistant or herbicide sensitive, and is phenotypically distinguishable from the second and third varieties.

As another alternative, a variety exhibiting resistance to a first herbicide can be formulated as the major proportion in a seed composition that contains second and third varieties, while a variety exhibiting resistance to a second, different herbicide can be formulated as the major portion in a seed composition that contains minor portions of a fourth variety and a fifth variety. The fourth variety can be sensitive to the second herbicide and phenotypically distinguishable from other varieties in the composition. The fifth variety can be resistant to the second herbicide and phenotypically distinguishable from the other varieties in the composition. The ratios of the major and minor varieties can be formulated as discussed herein.

It is known that planting seed is sometimes not sold in the year following its production. It is also known that the germination percentage of unplanted seed declines over time. In another aspect, the present invention allows an estimation of the year in which planting seed was intended to be sold, using seed compositions having one or more minor varieties. A seed composition can be formulated for a given geographic area with first and second varieties that are phenotypically distinguishable from each other on the basis on an initial set of phenotypic differences. In a subsequent growing season, a second seed composition is formulated for the same geographic area so that the first and second varieties are phenotypically distinguishable from each other on the basis of a set of phenotypic differences other than the initial set of phenotypic differences. The subsequent growing season can be the next growing season, two growing seasons later, or three or more growing seasons later. As an example, a seed composition in a first growing season can constitute from about 85% to 99.9% seeds of a 3L green, herbicide-resistant variety as a major variety of the composition and from about 0.1% to about 15% seeds of a 3LY, herbicide-sensitive variety as the minor variety. In a subsequent second, growing season, a second seed composition can have seeds of the same major variety and seeds having a 5LY, herbicide-sensitive phenotype as the minor variety. The use of different phenotypic markers for a minor variety in different growing seasons can be extended to third, fourth or even later growing seasons. For example, in a third growing season, a third seed composition can have seeds of the same major variety and seeds having a 7L variegated, herbicide-sensitive phenotype as the minor variety. It will be appreciated that a seed composition having first and second varieties is sufficient to achieve the goal of alternating phenotypic markers. However, it is understood that seed compositions having first, second and third varieties are also suitable.

Seed compositions having different phenotypic markers in different growing seasons can be useful to farmers and agricultural companies, since it permits an approximate date of production of a seed composition to be assigned to a group of plants in a field. That is, an approximate date can be assigned as to the growing season in which the seed composition was intended to be planted and thereby the approximate age of the composition.

The invention is further described in the following examples, which do not limit the scope of the invention described in the claims.

EXAMPLES

Example 1

Soybean Varieties

Soybean cultivars are bred using standard breeding practices to create varieties having the combinations of phenotypic markers described in Table 1. A yellow leaf phenotypic marker can be incorporated from, for example, the T135 strain, available from the U.S. Department of Agriculture (USDA) soybean germplasm collection. The T135 strain carries the y9 allele, which confers a bright greenish yellow color to leaves. A heptafoliate phenotypic marker can be incorporated from, for example, the T255 strain, available from the USDA. The T255 strain carries the lf2 allele, which confers a 7-foliate phenotype to leaves. A variegated leaf phenotypic marker can be incorporated from, for example, the T312 strain, available from the USDA. The T312 strain carries the v2 allele, which confers a variegated phenotype to leaves. A narrow, rugose leaflet phenotypic marker can be incorporated from, for example, the T313 strain, available from the USDA. The T313 strain carries the lnr allele, which confers a rugose phenotype to leaves.

Some of the criteria used to selecting cultivars include: seed yield, lodging resistance, emergence, disease resistance, maturity, late season plant intactness, plant height and shattering resistance. Breeders seed is entered in yield tests at several locations in the Midwest United States.

Cultivars typically show uniformity and stability, as described in the following variety description information. It is self-pollinated a sufficient number of generations with careful attention to uniformity of plant type. The variety is increased with continued observation for uniformity.

Maturity Date. Plants are considered mature when 95% of the pods have reached their mature color. The number of days is either calculated from August 31 or from the planting date.

Seed Yield (Bushels/Acre). The yield in bushels/acre is the actual yield of the grain at harvest.

Lodging Resistance. Lodging is rated on a scale of 1 to 5. A score of 1 indicates erect plants. A score of 2.5 indicates plants are leaning at a 45° angle in relation to the ground and a score of 5 indicates plants are laying on the ground.

*Phytophthora* Tolerance/resistance. *Phytophthora* root rot tolerance is rated on a scale of 1 to 5, with a score of 1 indicating the best or highest tolerance, and a score of 5 indicating no tolerance to *Phytophthora*. Plants can be *Phytophthora* resistant or sensitive, and those that are *Phytophthora* resistant have nucleic acid resistant genes such as, for example, Rps1k and Rps1c.

Emergence. This score indicates the ability of the seed to emerge when planted 3" deep in sand and with a controlled temperature of 25° C. The number of plants that emerge each day is counted. Based on this data, each genotype is given a 1 to 5 score based on its rate of emergence and percent of emergence. A score of 1 indicates an excellent rate and percent of emergence, an intermediate score of 2.5 indicates average ratings and a 5 score indicates a very poor rate and percent of emergence.

Iron-Deficiency Chlorosis. Plants are scored 1 to 5 based on visual observations. A score of 1 means no stunting of the plants or yellowing of the leaves and a score of 5 indicates the plants are dead or dying caused by iron-deficiency chlorosis, a score of 2.5 means plants have intermediate health with some leaf yellowing.

Brown Stem Rot. This is a visual disease score from 1 to 5 comparing all genotypes in a given test. The score is based on leaf symptoms of yellowing and necrosis caused by brown stem rot. A score of 1 indicates no symptoms. Visual scores range to a score of 5 that indicates severe symptoms of leaf yellowing and necrosis.

Shattering. The amount of pod dehiscence prior to harvest. Pod dehiscence involves seeds falling from the pods to the soil. This is a visual score from 1 to 5 comparing all genotypes within a given test. A score of 1 means pods have not opened and no seeds have fallen out. A score of 2.5 indicates approximately 50% of the pods have opened, with seeds falling to the ground and a score of 5 indicates 100% of the pods are opened.

Plant Height. Plant height is taken from the top of soil to top node of the plant and is measured in inches.

Seed Protein Peroxidase Activity. Seed protein peroxidase activity is defined as a chemical taxonomic technique to separate cultivars based on the presence or absence of the peroxidase enzyme in the seed coat. Generally, there are two types of soybean cultivars, those having high peroxidase activity (dark red color) and those having low peroxidase activity (no color).

Quantitative Trait Loci (QTL). Quantitative trait loci (QTL) refer to genetic loci that control to some degree numerically representable traits that are usually continuously distributed.

A number of embodiments of the invention have been described. Nevertheless, it will be understood that various modifications may be made without departing from the spirit and scope of the invention. Accordingly, other embodiments are within the scope of the following claims.

| REFERENCES: | |
| --- | --- |
| U.S. Pat. No. 5,004,864 | U.S. Pat. No. 5,706,603 |
| U.S. Pat. No. 5,704,160 | U.S. Pat. No. 5,994,621 |
| U.S. Pat. No. 5,859,349 | |

What is claimed is:

1. An article of manufacture, comprising:
(a) packaging material; and
(b) plant seeds within said packaging material, wherein said article is formulated to contain about 90 to about 99.8 percent seeds of a first variety of a plant species, about 0.5 to about 5 percent seeds of a second variety of the plant species, and about 0.5 to about 5 percent seeds of a third variety of the plant species, wherein plants of said first variety and said third variety exhibit resistance to the same herbicide, wherein plants of said second variety exhibit sensitivity to said herbicide, and wherein said plants of said first, second, and third varieties are phenotypically distinguishable from each other.

2. The article of claim 1, wherein said article comprises about 95 to about 99.5 percent seeds of said first variety.

3. The article of claim 1, wherein said article comprises about 97 to about 99.5 percent seeds of said first variety.

4. The article of claim 1, wherein said plants of said first and said third varieties exhibit resistance to glyphosate.

5. The article of claim 1, wherein said plants of said first and said third varieties exhibit resistance to glufosinate.

6. The article of claim 1, wherein said plants of said first and said second varieties are phenotypically distinguishable from each other on the basis of leaf color.

7. The article of claim 1, wherein said plants of said second and said third varieties are phenotypically distinguishable from each other on the basis of the number of leaves per peiole.

8. The article of claim 1, wherein the relative maturity of plants of at least on of said varieties differs from the relative maturity of plants of at least on other of said varieties.

9. The article of claim 1, wherein seeds of at least one of said varieties have a seed coat color that differs from the seed coat color of at least one other of said varieties.

10. The article of claim 9, wherein seeds of said first and said third varieties have the same seed coat color, and seeds of said second variety have a seed coat color that differs from the seed coat color of said first and third varieties.

11. The article of claim 1, wherein seeds of at least one of said varieties has microparticles adhered thereto.

12. the article of claim 11, wherein said microparticles are dual color microparticles.

13. The article of claim 1, wherein said article comprise about 93 to about 99.5 percent seeds of a first variety, about 0.5 to about 3 percent seeds of a second variety, and about 0.5 to about 3 percent seeds of a third variety.

14. The article of claim 1, wherein said article comprise about 95 to about 98.5 percent seeds of a first variety, about 0.5 to about 2 percent seeds of a second variety, and about 0.5 to about 2 percent seeds of a third variety.

15. A method for determining whether a group of crop plants was grown from a first generation seed composition or a second generation seeds composition, said method comprising:
determining that said group of crop plants was grown from a first generation seed composition that comprises about 90 to about 99.8 percent seeds of a first variety, about 0.1 to about 5 percent seeds of a second variety and about 0.1 to about 5 percent seeds of a third variety when the expected proportion of a phenotypic marker associates with said second variety and the expected proportion of a phenotypic marker associated with said third variety are observed in said group of crop plants, said determining occurring prior to application of a herbicide to said group of crop plants, wherein plants of said first variety and said third variety exhibit resistance to said herbicide and are phenotypically distinguishable from each other, and wherein said second variety exhibits sensitivity to said herbicide and is phenotypically distinguishable from said first and third varieties; or
determining that said group of crop plants was grown from a second generation seed composition that comprises about 90 to about 99.95 percent seeds of said first variety, and about 0.05 to about 10 percent seeds of said third variety when significantly less than the expected proportion of a phenotypic marker associated with said second variety and the expected proportion of a phenotypic marker associated with said third variety are observed among said group of crop plants, said determining occurring prior to application of said herbicide to said group of crop plants.

16. A method for determining whether a group of crop plants has received an application of herbicide, comprising:
  (a) determining that said crop plants, grown from seeds comprising about 90 to about 99.8 percent seeds of a first variety, about 0.1 to about 5 percent seeds of a second variety and about 0.1 to about 5 percent seeds of a third variety have not received an effective application of herbicide when the expected percentage of said crop plants have a phenotypic marker associated with said second variety and the expected percentage of said plants have a phenotypic marker associated with said third variety, wherein plants of said first variety and said third variety exhibit resistance to the same herbicide and are phenotypically distinguishable from each other, and plants of said second variety exhibit sensitivity to said herbicide and are phenotypically distinguishable from said first and third varieties; or determining that said crop plants grown from said seeds have received an effective application of herbicide when significantly less than the expected percentage of said crop plants have a phenotypic marker associated with said second variety and the expected percentage of said crop plants have a phenotypic marker associated with said third variety.

* * * * *

UNITED STATES PATENT AND TRADEMARK OFFICE
CERTIFICATE OF CORRECTION

PATENT NO. : 8,575,429 B2  
APPLICATION NO. : 13/196456  
DATED : November 5, 2013  
INVENTOR(S) : Gregory St. Clair Page 1 of 1

It is certified that error appears in the above-identified patent and that said Letters Patent is hereby corrected as shown below:

Title Page, item [73] Assignee, delete "Protection" and insert --Production-- therefor;

Title Page, item [56] Column 2 (Other Publications), delete "Retrived" and insert --Retrieved-- therefor;

In the Claims

Column 16, line 17 (Claim 7), delete "peiole" and insert --petiole-- therefor;

Column 16, line 21 (Claim 8), delete "on" and insert --one-- therefor;

Column 16, line 31 (Claim 12), delete "the" and insert --The-- therefor;

Column 16, line 50 (Claim 15), delete "associates" and insert --associated-- therefor.

Signed and Sealed this
Twentieth Day of May, 2014

Michelle K. Lee
*Deputy Director of the United States Patent and Trademark Office*